(12) United States Patent
Biegun et al.

(10) Patent No.: US 10,350,086 B2
(45) Date of Patent: Jul. 16, 2019

(54) IMPACTION DEVICE FOR AN INSERT ELEMENT

(71) Applicant: XNOV IP, Luxembourg (LU)

(72) Inventors: Jean-François Biegun, Porrentruy (CH); Frédérique Biegun, Porrentruy (CH); Pascal Loehle, Porrentruy (CH)

(73) Assignee: XNOV IP, Luxembourg (LU)

( * ) Notice: Subject to any disclaimer, the term of this patent is extended or adjusted under 35 U.S.C. 154(b) by 941 days.

(21) Appl. No.: 14/640,320

(22) Filed: Mar. 6, 2015

(65) Prior Publication Data

US 2015/0250616 A1    Sep. 10, 2015

(30) Foreign Application Priority Data

Mar. 7, 2014   (FR) ..................... 14 00563

(51) Int. Cl.
*A61F 2/46*    (2006.01)
*A61F 2/34*    (2006.01)
*A61F 2/30*    (2006.01)

(52) U.S. Cl.
CPC ............. *A61F 2/4609* (2013.01); *A61F 2/34* (2013.01); *A61F 2/4637* (2013.01); *A61F 2002/30558* (2013.01); *A61F 2002/30565* (2013.01); *A61F 2002/4623* (2013.01); *A61F 2002/4627* (2013.01); *A61F 2002/4681* (2013.01)

(58) Field of Classification Search
CPC .................. A61F 2/4609; A61F 2/4637; A61F 2002/4681; A61B 2017/925; A61B 2017/924; A61B 2017/922; F41B 7/003; B25C 1/143
See application file for complete search history.

(56) References Cited

U.S. PATENT DOCUMENTS

| 5,735,855 | A | 4/1998 | Bradley |
| 9,005,213 | B2* | 4/2015 | Fortin ............... A61B 17/1604 |
| | | | 606/100 |
| 9,289,313 | B2* | 3/2016 | Preuss ................... A61F 2/4637 |
| 2005/0165403 | A1* | 7/2005 | Miller .................. A61B 10/025 |
| | | | 606/79 |
| 2013/0204264 | A1 | 8/2013 | Mani et al. |

FOREIGN PATENT DOCUMENTS

| EP | 0 931 523 A1 | 7/1999 |
| EP | 1 190 687 A1 | 3/2002 |
| EP | 1 707 160 A1 | 10/2006 |
| EP | 2 422 754 A1 | 2/2012 |
| WO | 2010/109327 A1 | 9/2010 |

OTHER PUBLICATIONS

French Search Report (Application No. FR 1400563) (2 pages—dated Aug. 14, 2014).

* cited by examiner

*Primary Examiner* — Suba Ganesan
(74) *Attorney, Agent, or Firm* — Renner Kenner Greive Bobak Taylor & Weber

(57) ABSTRACT

Device for inserting an insert (1), made in particular of ceramic material, into a cup designed to be received in the cotyl of a hip, characterised in that it comprises: means (17, 20, 21, 22) for gripping the insert, in particular an upper free edge of the insert; a rod (5,6) designed to impinge on the insert when it is held by the gripping means opposite the hollow part of the cup; and means (32, 33, 34) for imparting a downwards shock to the rod to push the insert into the cup, i.e. introduce it by force to the inside of the cup, said shock imparting means imparting a shock to the rod with a predetermined force.

18 Claims, 4 Drawing Sheets

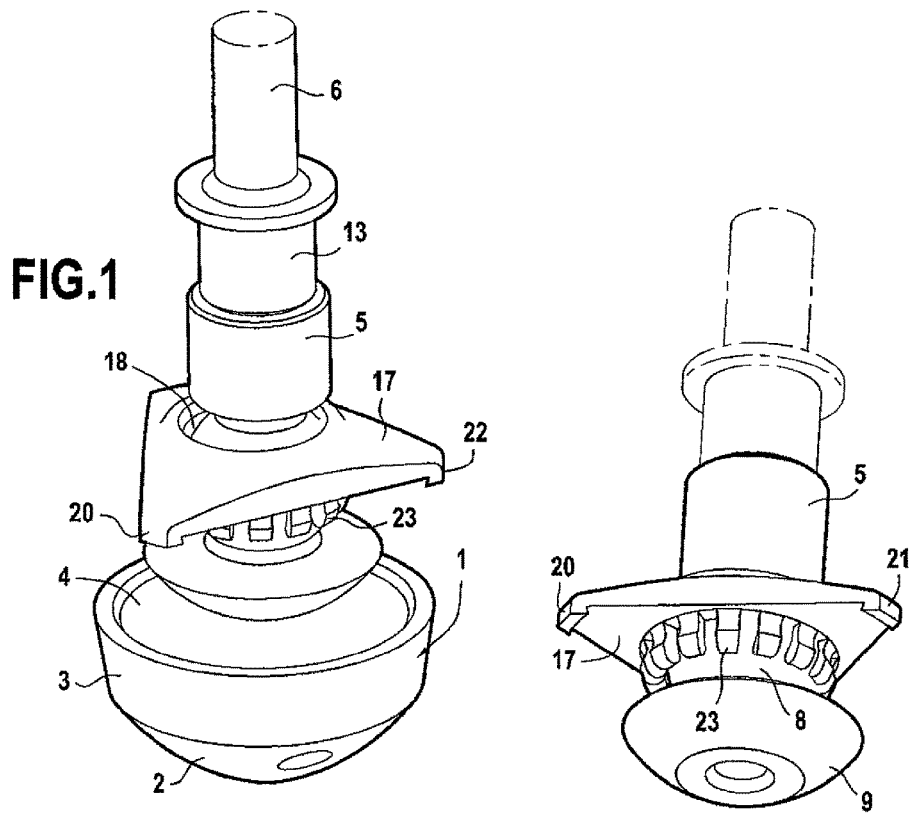
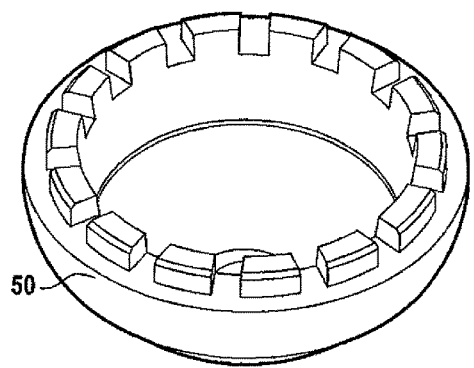

IMPACTION DEVICE FOR AN INSERT ELEMENT

TECHNICAL FIELD

The present invention relates to a said "impacting" device for "impacting" a rod, ie for imparting a shock thereto, said stem being destined to transmit said shock to an insert element to insert the latter into a reception element, for example an insert element, made in particular of ceramic material, into a cup which is itself designed to be received in the cotyloidal cavity of a hip of a patient. The present invention also relates to an assembly comprising an impacting device of this type and at least one rod destined for transmitting the shock to an insert element.

BACKGROUND ART

An impacting device for impacting with a predetermined force or power a spherical head so that it covers a rod, the impact occurring after positioning the head above the rod with the latter introduced slightly into the cavity of the head designed to receive it.

Said devices of the prior art do not make it possible to perform a precise impaction of the rod which transmits the shock to the insert, and it is frequent that the insert be not well inserted in the reception element or be deteriorated, in particular cracked, or even broken, in particular in case of using such impacters to insert a ceramic insert in a cup to be received in the cotyloidal cavity of a hip.

SUMMARY OF THE INVENTION

The present invention proposes overcoming the disadvantages of the prior art by proposing an impacting device of a rod which is destined to transmit a shock to an insert element to be inserted in a reception element which enables with certainty the correct insertion of the insert into the reception element, notably a cup, without damaging the latter, in particular without cracking it, breaking or moving it askew.

According to the invention, a device for impacting is as defined in claim 1.

In the present invention, the surgeon can grasp the impacting device with his full hand, ie with at least the four fingers of one hand in contact with the pistol type grip, on a same and only side, below the barrel, so as to be able both to easily orient the barrel by aiming with one's eye without the latter being obstrued, notably by handling means, and to be able to have one's forearm in line with the back of the palm of the hand so as to be able to apply a high pressure of the barrel against the rod.

By providing such gripping means of the impacting device which allow the surgeon not only to orient well the axis of the barrel and therefore the rod axis relative to the insert but also to apply a strong pushing force of the barrel against the rod to avoid loss of energy or power at the interface between the plunger and the rod, one makes sure that the theoritical predetermined force or power in term of value as well as in term of direction is conveniently applied to the rod and to the insert. One therefore avoids that the transmitted shock to the insert be insufficient for its good insertion in the cup, the effective imparted shock to the insert in prior art devices being always less than the theoritical shock because of the losses at the level of the interface impacter-rod and of the wrong alignment of the impacter and/or of the rod relative to the insert.

Improvements are defined in subclaims 2 to 9.

The present invention also relates to an assembly as defined in one of claims 10 to 14.

By thus providing means for holding the insert while it is impacted, it is possible, according to data and/or experience, to adjust the power of the shock to optimise the strike on the insert for the insertion thereof. During the shock the insert is not able to rotate slightly, so that the predefined effective value of the force of impact is conferred perfectly and is therefore reproduced and reproducible, contrary to the proposals of the prior art, for example in particular EP 1190687, in which the fact of not being held by holding means during the application of shock means that the axis of application of the shock or impact can vary from one shock to another and consequently affect the reproducibility of the impact, which in theory has a constant value but in practice does not. In EP 1 190 687, this disadvantage is exacerbated by the fact that the shock is applied to the spherical head receiving the insert and not to the insert. In this way variations in power are avoided, caused either by the practitioner and/or his form of the day, either as a result of a concurrent movement of the impacted insert, likely to involve either the cracking or breaking of the insert or the cup, or an incomplete insertion of the insert into the cup.

In this way an insertion device is obtained by impaction which makes it possible to perform said insertion in a particularly reliable and simple manner, by reducing to a very large degree the risk of "off-axis" insertion, which will potentially cause the breaking or cracking of the cup when placed in the cotyl. Regardless of the angle of force making the impaction relative to the insert, i.e. the orientation of the rod relative to the insert, the latter being held by the insertion device with the option of pivoting is always positioned perfectly in relation to the cup, regardless of the orientation of the rod relative to the cup, such that the surgeon no longer needs, as in the prior art, to ensure that the rod is perfectly perpendicular to the plane of the base of the cup during the insertion.

Preferably, the pivot point for pivotably mounting the gripping means relative to the rod-impaction head assembly is located substantially in the centre of the inner sphere of the insert.

According to a preferred embodiment of the invention, the gripping means of the insert are formed by a holding grip comprising at least two, preferably three, feet designed to fit closely around the insert in an elastically releasable manner.

Preferably, the holding grip comprises a base plate with feet projecting from the periphery thereof.

In particular, the base plate is pierced by a hole, in particular substantially centrally, the surface of the inner wall of which fits the form of a ball joint formed on the rod to enable the relative pivoting of the rod and the base plate.

According to an advantageous embodiment, the distal end of the rod comprises a head projecting laterally from the rod and forming the impact head, the head having a distal end surface, particularly in the form of a dome, designed to fit in part with the form of the base of the inner cavity of the insert.

The present invention also relates to a kit as defined in claim 15.

According to one refinement, also forming an invention in itself independently of the invention described above, means are provided for imparting a downwards shock to the rod to impact the insert into the cup, i.e. introduce it by force to the inside of the cup, said shock imparting means imparting a shock to the rod with a predetermined force.

According to a preferred embodiment of the invention, the imparting means comprise a plunger and a spring.

Preferably, the imparting means comprise means for displacing the plunger against the compression of the spring so as to compress the spring and means for locking the plunger in a position in which the spring is compressed and means, in particular in the form of a trigger, for releasing the plunger, the release of the plunger involving its instantaneous displacement owing to the decompression of the spring and its predetermined action on the rod, imparting to the latter the predetermined power shock.

Preferably, the spring and the plunger are received in a cavity formed upstream of the rod.

Preferably, the cavity receiving the plunger and the spring is formed in a body arranged upstream of the rod, in particular a body in one piece with the rod.

Preferably a grip, in particular in the form of a pistol grip, projects from the body.

BRIEF DESCRIPTION OF THE DRAWINGS

In the following, by way of example, embodiments of the invention are described with reference to the drawings, wherein:

FIG. 1 is an insertion device according to the invention, a cup and an insert made of ceramic material designed to be inserted by the insertion device inside the cup 50;

FIG. 3 is a perspective view from below of part of the insertion device of FIG. 1;

PREFERRED EMBODIMENT FOR CARRYING OUT THE INVENTION

Figure 2C:
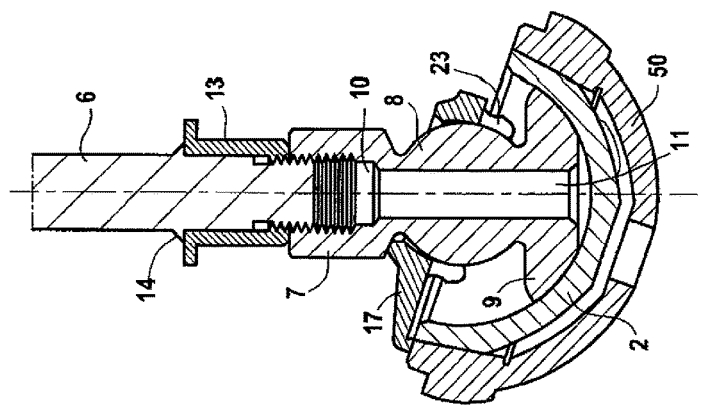
FIGS. 2A, 2B and 2C represent the different stages of inserting the insert into the cup by means of the insertion device.

FIG. 1 in perspective view shows an insertion device according to an embodiment of the invention of an insert 1 made of ceramic material in a cup 50. The insert 1 made of ceramic material is formed by a ceramic body, in particular made of alumina ceramic material, with an exterior surface in the form of a spherical cap 2 terminated by a part 3 of the upper or proximal edge with a slightly truncated cone shape. The insert is hollow and comprises an inner cavity 4 the wall of which has a hemispherical form. In particular, the inscribed cone of the truncated cone part 3 of the edge of the outer surface of the insert forms an angle of about 3 to 5° relative to the vertical axis of symmetry of the insert made of ceramic material.

The insertion device is formed by a circular cylindrical rod 6 to which an impact end piece 5 has been adapted at its distal end. The end piece 5 comprises a tubular proximal section 7 which is tapped to receive the threaded end of the rod 6 therein, to thus join the latter by screw connection. It is possible instead to ensure that the end piece is held with the rod by means of another type of connection, for example a clipping system. It is also possible for the end piece to be in one piece with the rod.

The end piece 5 then comprises an intermediate section in the form of a spherical ball 8 and a distal section forming the impaction head 9. The impaction head 9 has a greater transverse dimension than the rest of the end piece 5, in particular than the proximal section 7, and its lower or distal surface is in the form of a dome being at least partly complementary to the inner surface of the cavity 4 of the insert 1, so as to be able to make surface contact with the latter. Conversely, it is also possible that the impaction head 9 has a smaller transverse dimension than the rest of the end piece 5, in particular than the proximal section 7.

The outer surface of the head 9 designed to be applied against the wall of the base of the cavity 4 is inscribed into a sphere, concentric to the sphere defining the ball 8. This facilitates the free orientation of the insert.

On the inside of the end piece 5, at the end of the proximal section 7 there is an abutment 10 against which the distal end of the rod 6 abuts, in order to block its screw connection with the internal tapping of section 7. Furthermore, a channel 11 opening to the lower surface in the form of a dome of section 9 by an opening facilitates the internal cleaning of the end piece.

A connecting element 13 which is also tubular terminates the connection between the end piece 5 and the rod 6. Said element 13 comprises a threaded end which screws into the part of the thread of the screw which does not cooperate with the tapping of the end piece 5. From the other proximal side the element 13 is welded at 14 to the rod.

An element forming a grip is mounted pivotably in relation to the ball 8. Said grip comprises a substantially plane plate 17, with a triangular form and with three tips from which three respective feet 20, 21 and 22 project. The feet are designed to fit around the insert on its upper or proximal edge. The feet and/or the plate are made from a material and/or have thickness such that they have a certain degree of elasticity which enables them to fit elastically around the upper edge of the insert 1 in an flexible manner and to release it when a deforming force is applied to the grip, for example by bearing on the plate 17. The plate 17 is pierced in its centre by a hole 18 with a shape complementary to the spherical ball 8 forming the ball joint and comprises elements 23 in the form of teeth which have substantially a form complementary to that of the spherical ball 8 so as to match the form. The material and/or the thickness of the teeth is (are) selected so as to enable the elastic clipping of the plate onto the ball joint. The inner edge of the hole 18 has an inner wall with a curved shape complementary to the form of the ball 8 forming the ball joint. The assembly is such that the plate 17, once clipped by teeth 23 to the ball joint 8, can pivot relative to the ball joint 8, and therefore relative to the connected rod 6 particularly in rotation of the ball joint 8.

In the embodiment shown three feet have been provided. However, it would also be possible to have more, in particular four or five for large inserts. It is also possible instead of feet to provide a disc that runs all around.

The dimension of the plate is such that when the head 9 is in contact with the surface of the internal wall of the insert made of ceramic material, the three feet 20, 21 and 22 fit around the free peripheral edge of the truncated cone part 3 of the insert 1 made of ceramic material, the three feet 20, 21 and 22 then extend towards the cup along the outer surface of the part 3 of the insert 1 made of ceramic material by fitting around the latter. The insert 1 made of ceramic material is thus held by the grip in an elastic manner.

Figure 2B:
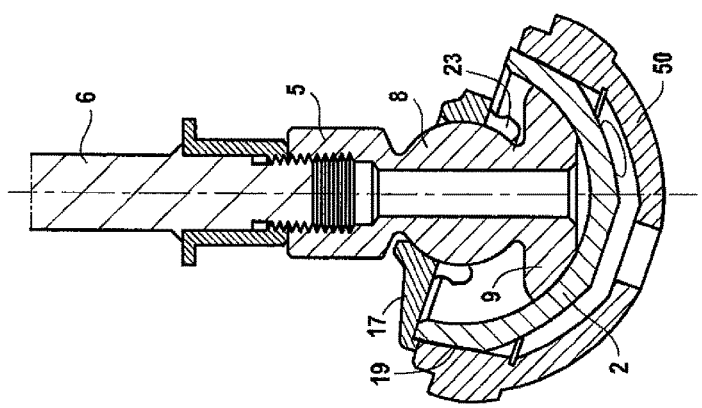
Figure 2A:
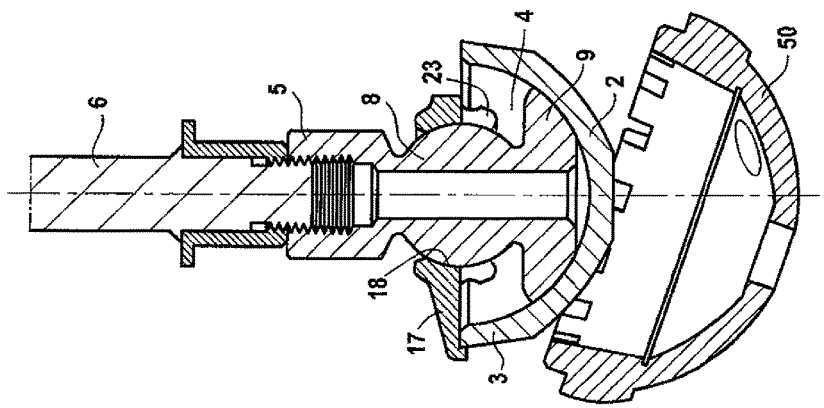

Once the insert is held between the feet 20, 21, 22 (FIG. 2A), the insert 1 is positioned by means of the device on the inside of the cup (FIG. 2B). This stage is performed without it being necessary for the insertion axis (the axis of the rod) to be perpendicular to the base plane or upper plane of the cup or insert, by the relative pivot mounting of the grip-insert assembly previously joined mutually by clamping the feet. This second stage of pushing takes place until the distal edges of the feet 20, 21 and 22 abut against the upper free edge of the cup. At this moment, the insert is largely introduced into the cup having its truncated cone part 3 almost in contact with the inner face of the cup, in an upper section 19 having a form complementary to this truncated cone element of the insert. The two truncated cone parts of the insert and the cup are therefore held in a coaxial position but are not connected since the feet maintain a minimum play between the insert and the cup. As a result the simple pushing of the insert into the cup comes to a stop almost at the same moment as the distal ends of the feet 20, 21, 22 come into contact with the free edge of the cup.

To then insert the insert into the cup by force, the surgeon applies a shock to the rod, for example by striking the top of the rod downwards in the direction of extension of the rod. Taking into account the flexibility of the feet and/or the plate, this shock simultaneously presses the insert into its final position in the cup (position represented in FIG. 2C) and releases the feet from their grip on the insert.

As the insert has been positioned by means of the device of the invention and centred perfectly relative to the cup in the position of FIG. 2B prior to the application of shock, it is not necessary for the rod to be perfectly perpendicular to the upper plane of the cup and the insert (in which planes the free edges of the cup and the insert extend respectively) during the application of this shock, the angle between the rod and the axis of the insert can in particular, as shown in FIG. 2C, have a greater value, for example 10 to 20°, without this having the least effect on the "quality" of the final insertion by force of the insert.

The relative locking of the insert in the cup is achieved by the slight difference in conicity of the inner walls 19 of the cup and 3 outer walls of the insert 1. However, it is also possible to achieve said adjustment of force in another way, for example by providing projections from the outer surface of the insert.

A first embodiment has been described above in which the surgeon applies the impaction shock by striking the rod.

It is possible, according to another advantageous embodiment, to provide at the proximal end of the rod 6 a part in the form of a pistol. Said part in the form of a pistol comprises a body 30 with a barrel 31 designed to be connected, in particular in a joined manner, to the rod 6. In the barrel 31 a cavity 32 is formed in which a plunger 33 is mounted to be movable in translation along the length of the axis of the barrel. A spring 34 is arranged at the rear of the plunger. A rod 36 joined to the plunger 33 passes through the spring and leaves the body 30 through a rear opening 50. The rod 36 enables the user, in particular by means of a ring 37 connected to the rod 36, to pull the plunger 33 to the rear thus compressing the spring 34 against a shoulder 51 of the plunger 33 until a transverse circular notch 38 is locked by clicking into an abutment 39. When the abutment 39 is locked into the notch 38, the plunger is displaced as far as possible to the rear and the spring 34 is compressed. The abutment 39 is mounted rotatably, such that a tail of a trigger 40, mounted rotatably, drives the rotation of the abutment 39 and therefore its exit from the notch 38 and lastly the release of the plunger 33. Under the effect of the charge of the precompressed spring, the plunger 33 is then displaced at high speed towards the left in FIG. 4 and hits the distal end of the cavity 32, entering into collision with the rod 6, the proximal end of which was previously introduced into an introduction channel 35 up to the distal opening 52 of the cavity 32. Locking means for the introduction of the rod into the barrel 31 can be provided so that the rod penetrates into the channel 35 but stops at the entry 52 of the cavity 32. Said locking means can for example be a circular abutment projecting laterally from the rod and abutting against the distal outlet opening of the canal 35.

The rod is then subjected to a shock which impinges on the insert made of ceramic material to insert it into the cup.

The device also comprises a grip 41 in the form of a pistol handle.

Thus the impaction force applied to the rod 6 can be determined in advance by the choice of spring 34, its rigidity and displacement path towards the rear of the plunger 33. In this way a constant impulsion force is ensured on the rod and thus a force or impaction power of the insert into the cup which is constant or substantially constant, corresponding exactly to that which is necessary to ensure the correct insertion of the insert, without the latter cracking, as was the case in the prior art where it was difficult to control the effort of the hammer. The speed imparted to the rod by the release of the plunger can be determined in advance by the choice of geometry of the constituent elements of the insertion device, in particular the spring, the plunger, the length of the tube 6 and the like.

Figure 4:
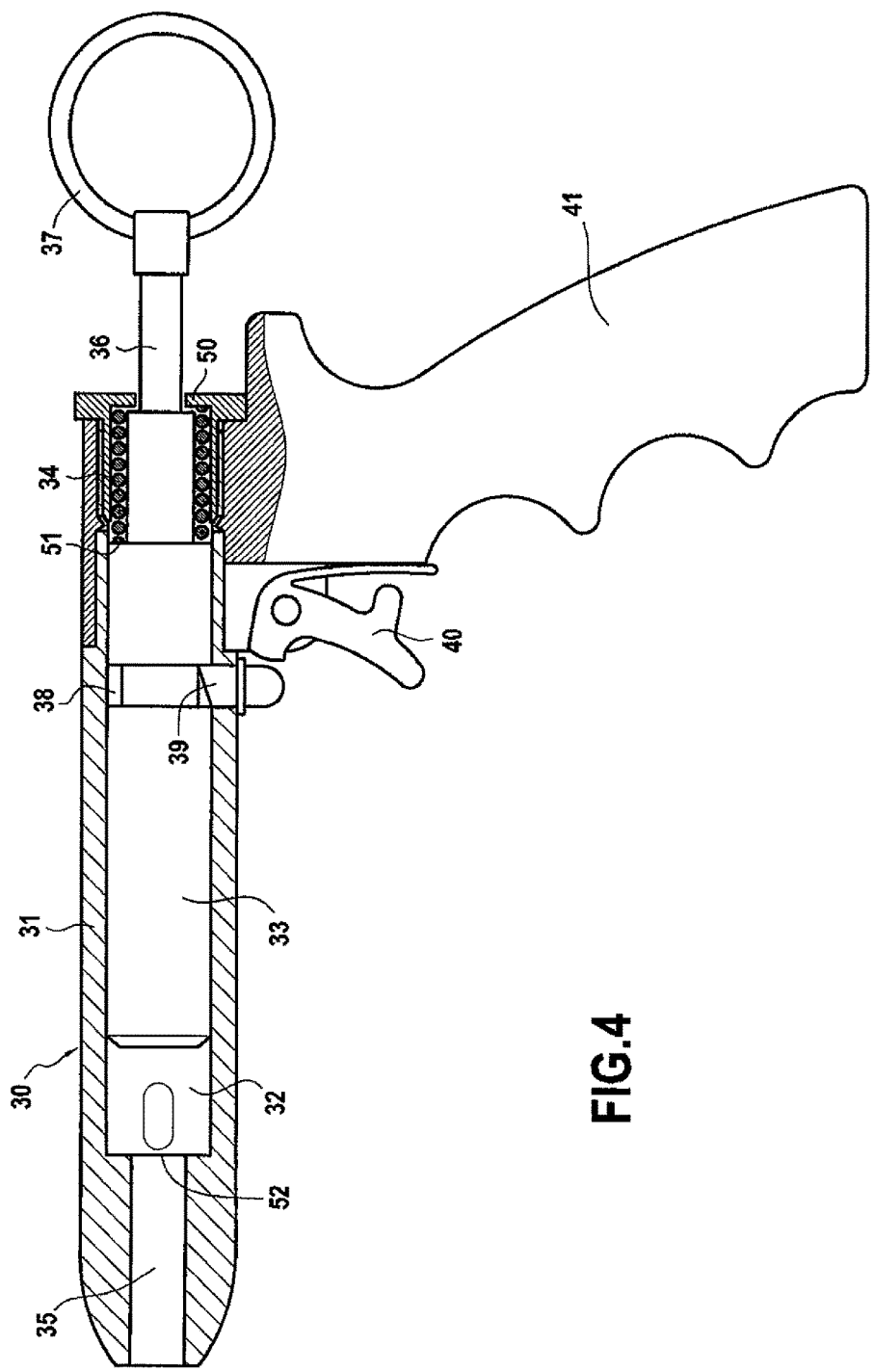
FIG. 4 is a perspective view of a device for "impacting" or for applying a shock to the rod of the insertion device of the preceding figures which, according to an advantageous embodiment, can be adapted to the insertion device of FIGS. 1 to 3.
Figure 5:
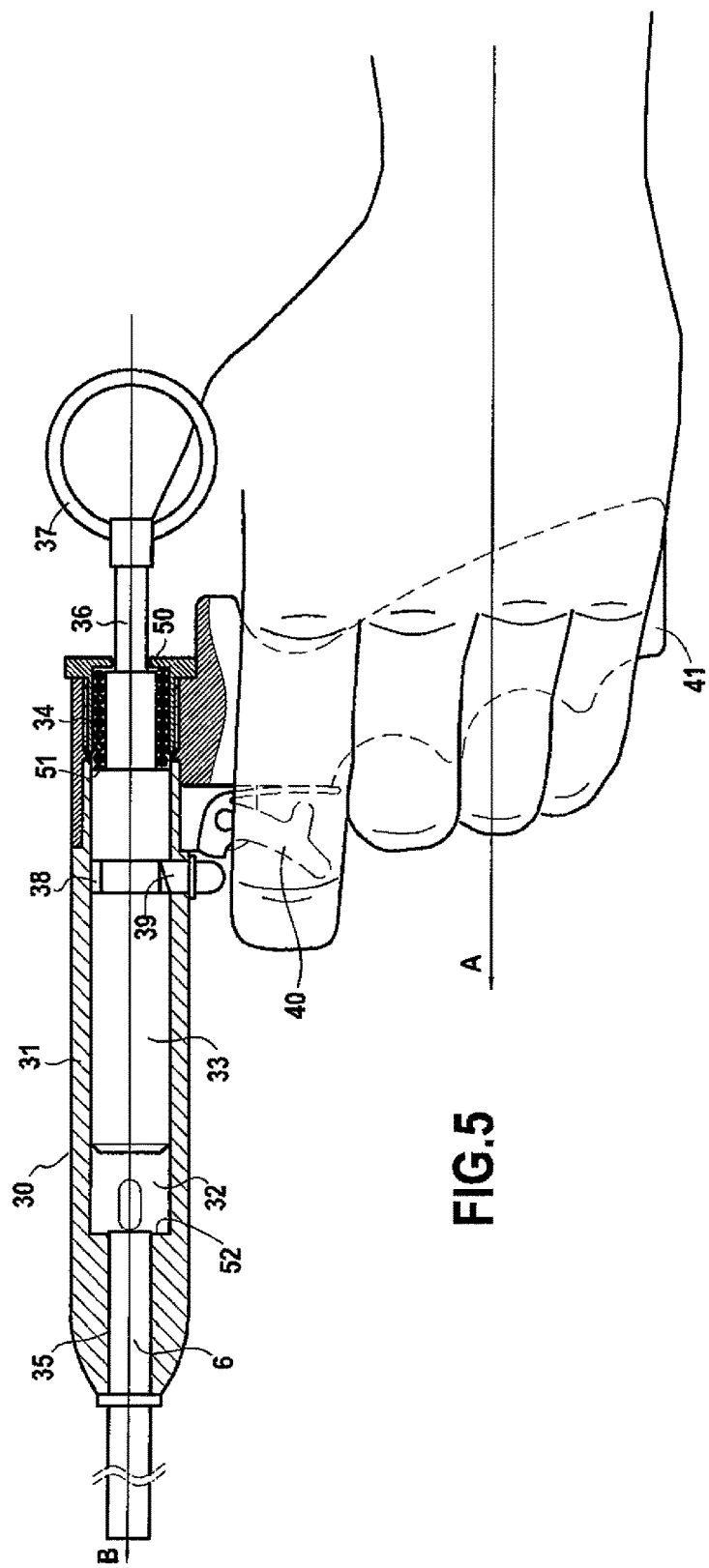
FIG. 5 is a view of the device of FIG. 4, as used by the surgeon, the rod inserted by the distal opening being possibly the one of the device shown in FIGS. 1 to 3.

In FIG. 5, one can see how the impacting device of FIG. 4 is used. The surgeon takes the device by hand by grabbing the pistol handle 41, said handle having a shape and a size such that when the surgeon holds it as it is normally provided for, like a pistol, his forearm and the back of the hand are mutually aligned, without the wrist being broken, and axis A of the forearm is substantially parallel to longitudinal axis B of the barrel. Furthermore, the four fingers of the hand can all be in contact simultaneously with the pistol handle, while all being on the same side of the barrel, ie under the barrel when the latter is pointing horizontally.

The surgeon can press the barrel of the pistol firmly against the rod to which he intends to impart a shock so as to make sure of a perfect positioning of the rod relative to the plunger, so that the latter deliver to the former a shock with the intended value and orientation, avoiding therefore losses or variations at the interface rod-plunger at the time of impact, and therefore avoiding a less than expected shock transmitted to the rod. Furthermore, it is easier for the surgeon to aim well at the point where he intends to apply the shock.

The present application describes the device for gripping and inserting the insert by means of the embodiment in FIGS. 1 to 3. However, the use of the automatic impaction device of FIGS. 4 and 5 is not connected to this embodiment and in particular it is possible to use it with any other type of gripping and insertion device, for example a device that only comprises a simple rod, joined to the insert or not, without the possibility of mutual pivoting, for example with the devices described in U.S. Pat. No. 4,994,064, EP-A-0931523, U.S. Pat. No. 5,462,548 or the like, without departing as such from the scope of protection of the invention defined by the present application.

What is claimed is:

1. An impacting device for imparting a shock on a rod used to transmit the shock to an insert element so as to insert the insert element in a reception element, the impacting device comprising:
   a body having a barrel defining an inner channel having
      a longitudinal axis and having a distal end opening adapted so that a proximal end of the rod can be inserted therein;

impacting means for imparting a predetermined shock pulse to the proximal end of the rod when the rod is inserted into said inner channel;

gripping means for allowing a user to grip said impacting device with at least one hand; and triggering means adapted to trigger said impacting means, wherein said gripping means are made in the form of a pistol grip, so that the user can take the impacting device with the at least one hand in contact with said pistol grip, on a first side, located below said barrel, and wherein said pistol grip and said triggering means are both disposed on said first side of said body located below said barrel.

2. The impacting device of claim 1, wherein stop means are provided within the barrel, so that during the imparting of the shock pulse to the rod by the impacting means, said barrel, under a force exerted by the user holding the device by the pistol grip, also exerts a pressure on the rod to press it against the insert element.

3. The impacting device of claim 2, wherein the stop means also prevents an end portion of the rod from being inserted into the barrel past the stop means.

4. The impacting device of claim 3, wherein said means for imparting a predetermined shock pulse to the rod comprise a plunger and a spring.

5. The impacting device of claim 4, wherein means are provided for displacing the plunger against the compression of the spring so as to compress the spring.

6. The impacting device of claim 4, wherein means are provided for locking the plunger in a charged position in which the spring is compressed, and means are provided for releasing the plunger, the release of the plunger causing instantaneous displacement of the plunger due to the decompression of the spring and the pulse action of the spring on the rod imparting to the latter said predetermined shock pulse.

7. The impacting device of claim 6, wherein the means for releasing the plunger is a trigger release.

8. The impacting device of claim 4, wherein said spring and said plunger are received in a cavity proximal to the rod, said end portion of the rod being maintained by said stop means distant from said plunger in a charged position.

9. The impacting device of claim 1, wherein the user can trigger said impacting means by acting on a trigger with a finger of the user's hand, while holding the pistol type grip having a forearm of the user aligned with the back of a palm of the hand and parallel to the longitudinal axis of said barrel.

10. The impacting device of claim 9, wherein the finger of the user's hand is the index finger of the user's hand.

11. An assembly comprising a device as defined in claim 1 and the rod, an end of the rod being inserted in the inner channel of the barrel by the distal end opening of the inner channel.

12. The assembly of claim 11, wherein there is also provided the insert element having insert gripping means located at a free upper edge of said insert element, said rod being destined to impact the insert element when the latter is held by said insert gripping means in front of hollow part of the reception element, wherein the reception element is a cup.

13. The assembly of claim 12, wherein the insert element comprises an impaction head with a surface designed to come into contact with at least a portion of an inner surface of a hollow part of the insert element, and the impaction head and the rod are connected to one another in a manner so as to be joined in rotation, wherein the impaction head emerges from the rod and the impaction head and rod are mounted pivotably relative to the insert gripping means.

14. The assembly of claim 11, wherein stop means are provided to prevent said rod from being inserted in the inner channel of the barrel beyond a proximal end portion of the rod.

15. The assembly of claim 14, wherein the stop means are made of a circular ring projecting laterally from the rod.

16. A kit comprising an assembly as defined in claim 11 and at least one insert, wherein the at least one insert is made of a ceramic material, and wherein the at least one insert is designed to be inserted into a cotyloidien cup.

17. The impacting device of claim 1, wherein said triggering means comprises a trigger and wherein said trigger is rotatably mounted.

18. The impacting device of claim 1, further comprising a pulling means provided to pull said impacting means to a charged position, said pulling means being on a second side of said body, wherein said second side is distinct from said first side.

* * * * *